(12) United States Patent
Zaima et al.

(10) Patent No.: US 8,236,982 B2
(45) Date of Patent: *Aug. 7, 2012

(54) PROCESS FOR PRODUCTION OF TEREPHTHALIC ACID

(75) Inventors: Fumiya Zaima, Okayama (JP); Masato Inari, Okayama (JP); Hideaki Fujita, Okayama (JP); Nobuo Namiki, Okayama (JP)

(73) Assignees: Mitsubishi Gas Chemical Company, Inc., Tokyo (JP); Toyobo Co., Ltd., Osaka-shi (JP); Mizushima Aroma Company, Ltd., Kurashiki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/048,644

(22) Filed: Mar. 15, 2011

(65) Prior Publication Data

US 2011/0213181 A1   Sep. 1, 2011

Related U.S. Application Data

(63) Continuation of application No. 12/518,662, filed as application No. PCT/JP2007/073650 on Dec. 7, 2007, now abandoned.

(30) Foreign Application Priority Data

Dec. 11, 2006   (JP) .................... 2006-333240

(51) Int. Cl.
  *C07C 51/16* (2006.01)
  *C07C 51/255* (2006.01)
(52) U.S. Cl. ....................................... 562/414
(58) Field of Classification Search .................. None
  See application file for complete search history.

(56) References Cited

U.S. PATENT DOCUMENTS

| 4,162,991 | A | 7/1979 | Jones |
| 4,238,294 | A | 12/1980 | Takeuchi et al. |
| 4,910,175 | A | 3/1990 | Michel et al. |
| 5,880,313 | A | 3/1999 | Zaima et al. |
| 2010/0016629 | A1 | 1/2010 | Zaima et al. |
| 2010/0048943 | A1 | 2/2010 | Zaima et al. |

FOREIGN PATENT DOCUMENTS

| JP | 48 66090 | 9/1973 |
| JP | 53 102290 | 9/1978 |

(Continued)

OTHER PUBLICATIONS

U.S. Appl. No. 13/048,537, filed Mar. 15, 2011, Zaima, et al.

*Primary Examiner* — Paul A Zucker
*Assistant Examiner* — Jennifer C Sawyer
(74) *Attorney, Agent, or Firm* — Oblon, Spivak, McClelland, Maier & Neustadt, L.L.P.

(57) ABSTRACT

A method for producing terephthalic acid comprising:
  subjecting a p-phenylene compound to a liquid-phase oxidation reaction by the use of a molecular-oxygen-containing gas in the presence of a catalyst at least containing a heavy metal compound and a bromine compound, and hydrous acetic acid having a water content of 1 to 15 mass %, to thereby yield a slurry;
  regulating the temperature of the slurry to 35 to 140° C., to thereby cause terephthalic acid to precipitate;
  removing the terephthalic acid through solid-liquid separation, to thereby recover a mother liquor; and
  recovering the catalyst from the mother liquor through a series of operations (1) to (4), as described, for reusing at least a portion of the catalyst in the liquid-phase oxidation reaction.

10 Claims, 1 Drawing Sheet

FOREIGN PATENT DOCUMENTS

| | | |
|---|---|---|
| JP | 53 102891 | 9/1978 |
| JP | 53 104590 | 9/1978 |
| JP | 53 133574 | 11/1978 |
| JP | 2 203939 | 8/1990 |
| JP | 10 15390 | 1/1998 |
| JP | 11 152246 | 6/1999 |
| JP | 2002 12573 | 1/2002 |
| JP | 2002 105018 | 4/2002 |
| JP | 2003 507160 | 2/2003 |

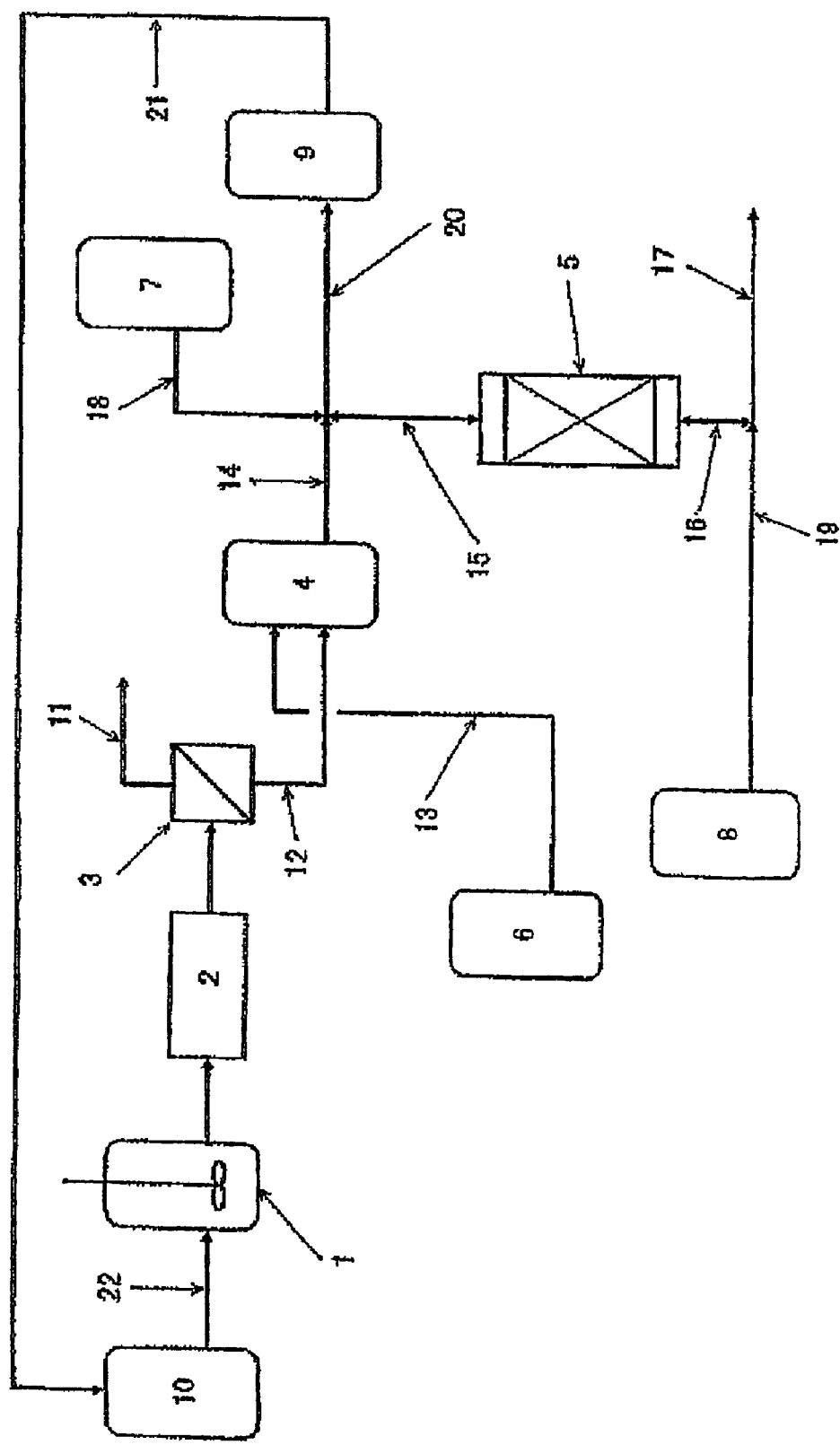

PROCESS FOR PRODUCTION OF TEREPHTHALIC ACID

TECHNICAL FIELD

The present invention relates to a method for producing terephthalic acid. Terephthalic acid is effectively employed as, for example, a starting material for polyethylene terephthalate.

BACKGROUND ART

Generally, terephthalic acid is produced through liquid-phase oxidation reaction of a p-phenylene compound (e.g., p-xylene) in acetic acid serving as a solvent in the presence of a catalyst (e.g., cobalt or manganese), or in the presence of a catalyst together with a promoter (e.g., a bromine compound or acetaldehyde). A slurry containing crude terephthalic acid produced through such liquid-phase oxidation reaction is generally subjected to crystallization at ambient pressure and lowered temperature, followed by solid-liquid separation.

A mother liquor recovered through the solid-liquid separation contains catalyst-derived useful catalyst components such as heavy metal ions and bromide ions, and an industrial process requires recycling of these catalyst components for reduction of production cost. In the most convenient recycling method, the mother liquor is returned, as it is, to and reused in the reaction system. However, as has been known, since the mother liquor contains, for example, various organic impurities by-produced through liquid-phase oxidation reaction, and inorganic impurities derived from corrosion of an employed apparatus, when the mother liquor is reused as it is in the reaction system, the concentration of these impurities is gradually increased in the reaction system, and an increase in impurity concentration beyond a predetermined level adversely affects liquid-phase oxidation reaction. For example, in the case of production of terephthalic acid, the mother liquor is generally returned to the reaction system in a proportion of 70 to 98%, and the remaining portion (2 to 30%) of the mother liquor (i.e., a portion of the mother liquor which is not reused in the reaction system) is fed to a step of recovering acetic acid serving as a solvent. In view of the foregoing, various methods have been proposed for recovering catalyst components from the mother liquor fed to such an acetic acid recovery step, and reusing the catalyst components.

For example, such known methods include a method in which water and an alkali metal carbonate salt are added to a residue obtained through recovery of a solvent from a mother liquor, to thereby cause a catalyst component in the form of carbonate salt to precipitate, and the catalyst component is dissolved in a predetermined amount of acetic acid serving as a solvent, and reused for reaction (see Patent Document 1); and a method in which oxalic acid and an alkali metal hydroxide are added to a mother liquor, to thereby cause a catalyst component in the form of oxalate salt to precipitate, and the catalyst component is dissolved in acetic acid serving as a solvent, followed by oxidation for recovery of the catalyst component (see Patent Document 2). There have also been known methods for recovering a catalyst component from a mother liquor by use of an anion exchange resin (see Patent Documents 3 to 11), including a method in which a bromide-ion-type anion exchange resin is exposed to a mother liquor for adsorption of cobalt ions and manganese ions on the resin, hydrous acetic acid having a water content of 2 mass % and water are caused to pass through the resin, to thereby recover cobalt ions and manganese ions through elution, a lower-aliphatic-monocarboxylate-ion-type weakly basic anion exchange resin is exposed to an eluate obtained through the aforementioned adsorption for adsorption of bromide ions and nickel ions on the resin, and hydrous acetic acid having a water content of 2 mass % and water are caused to pass through the resin, to thereby recover bromide ions and nickel ions through elution (see Patent Document 3); a method in which the cobalt concentration and the bromine/cobalt ratio of a mother liquor are respectively regulated so as to fall within specific ranges, followed by adsorption of cobalt and bromine on a strongly basic anion exchange resin, and cobalt and bromine are eluted from the strongly basic anion exchange resin with hydrous acetic acid having a water content of 10 mass % or more, to thereby recover a cobalt catalyst (see Patent Document 4); a method in which cobalt ions, manganese ions, and bromide ions are caused to be adsorbed together on an anion exchange resin containing a pyridine ring serving as an ion exchange group, and these ions are recovered through elution by a known technique (see Patent Document 5); and a method in which a catalyst component is recovered from a mother liquor by use of an anion-exchange-type chelate resin (see Patent Document 7).

Patent Document 1: Japanese Patent Application Laid-Open (kokai) No. S48-066090
Patent Document 2: Japanese Patent Application Laid-Open (kokai) No. H02-203939
Patent Document 3: Japanese Patent Application Laid-Open (kokai) No. S53-104590
Patent Document 4: Japanese Patent Application Laid-Open (kokai) No. S53-133574
Patent Document 5: Japanese Patent Application Laid-Open (kokai) No. S53-102290
Patent Document 6: Japanese Patent Application Laid-Open (kokai) No. H10-015390
Patent Document 7: Japanese Patent Application Laid-Open (kokai) No. H11-152246
Patent Document 8: Japanese Patent Application Laid-Open (kokai) No. 2002-012573
Patent Document 9: Specification of U.S. Pat. No. 4,162,991
Patent Document 10: Specification of U.S. Pat. No. 4,238,294
Patent Document 11: Japanese Kohyo Patent Publication No. 2003-507160

DISCLOSURE OF THE INVENTION

Problems to be Solved by the Invention

The method described in Patent Document 1 or 2 requires, for example, an alkali metal carbonate salt or oxalic acid in an amount equivalent to or greater than that of a catalytic metal, and thus is economically disadvantageous. In addition, the method requires an intricate process and a great deal of labor for recovery of a catalyst component in the form of carbonate salt or oxalate salt, which is not preferred.

The anion exchange resins described in Patent Documents 3 to 6 and 8 to 11 exhibit low heat resistance (allowable temperature limit: 80 to 100° C.), and thus may undergo chemical degradation (reduction in exchange capacity) or physical degradation (e.g., breakage of the resin) depending on the temperature of a mother liquor which has been caused to pass through the resins, which is not preferred. When a pyridine-ring-containing anion exchange resin described in Patent Document 5 is employed, elution of cobalt ions, manganese ions, and bromide ions adsorbed on the resin requires a liquid containing, for example, sulfuric acid, nitric acid, alkylsulfuric acid, or hydroxide ions, and, in practice, difficulty is encountered in reusing the thus-recovered liquid as is in the reaction system.

The method described in Patent Document 7 employs an anion-exchange-type "chelate resin," and is advantageous in that, unlike the case of the pyridine-ring-containing anion exchange resin described in Patent Document 5, cobalt ions, manganese ions, and bromide ions adsorbed on the chelate resin can be eluted with hydrous acetic acid having a water content of 1 to 15 mass %. However, when a mother liquor recovered through the method of the present invention (i.e., a mother liquor recovered through solid-liquid separation of a slurry produced by liquid-phase oxidation reaction of a p-phenylene compound) is caused to pass through the chelate resin, a carboxylic acid mixture which has been by-produced (hereinafter may be referred to as a "by-produced carboxylic acid mixture") is adsorbed on the chelate resin, and, upon elution of cobalt ions, manganese ions, and bromide ions, the by-produced carboxylic acid mixture is eluted and recovered together with these ions. When the by-produced carboxylic acid mixture concentration of the mother liquor is increased, a catalyst is deactivated, and reaction yield is reduced. Therefore, a catalyst recovery method employing the anion-exchange-type chelate resin has not yet been put into practice on an industrial scale.

In view of the foregoing, an object of the present invention for solving the aforementioned problems is to provide a method for producing, in an industrially advantageous manner, terephthalic acid by use of a specific chelate resin while suppressing an increase in concentration of a by-produced carboxylic acid mixture in a reaction system and a mother liquor.

Means for Solving the Problems

In order to attain the aforementioned object, the present inventors have conducted extensive studies, and as a result have found that, in the production of terephthalic acid, when catalyst components are recovered from a mother liquor by use of an anion-exchange-type pyridine-ring-containing chelate resin through a series of the below-described steps (1) to (4), heavy metal ions and bromide ions (i.e., catalyst components) can be separated from a by-produced carboxylic acid mixture, and, even in the case where liquid-phase oxidation reaction is carried out continuously, an increase in concentration of the by-produced carboxylic acid mixture can be suppressed in the reaction system and the mother liquor, and therefore the catalyst components can be recovered and reused a maximum number of times in liquid-phase oxidation reaction without being deactivated. The present invention has been accomplished on the basis of this finding.

Accordingly, the present invention provides:

[1] a method for producing terephthalic acid, characterized by comprising:

subjecting a p-phenylene compound to liquid-phase oxidation reaction by use of a molecular-oxygen-containing gas in the presence of a catalyst at least containing a heavy metal compound and a bromine compound, and hydrous acetic acid having a water content of 1 to 15 mass %, to thereby yield a slurry;

regulating the temperature of the slurry to 35 to 140° C., to thereby cause terephthalic acid to precipitate;

removing the terephthalic acid through solid-liquid separation, to thereby recover a mother liquor; and recovering the catalyst from the mother liquor through a series of the following steps (1) to (4) for reusing at least a portion of the catalyst in the liquid-phase oxidation reaction:

(1) an adsorption step including regulating the ratio "amount by mole of bromide ions in the mother liquor/total amount by mole of heavy metal ions in the mother liquor" to 0.6 to 3, and then exposing the mother liquor to a pyridine-ring-containing chelate resin which has been heated to 35 to 140° C., so that the resin adsorbs catalyst-derived heavy metal ions and bromide ions, and also adsorbs a carboxylic acid mixture which has been by-produced through the liquid-phase oxidation reaction (hereinafter the carboxylic acid mixture will be referred to as a "by-produced carboxylic acid mixture"), (2) an elution step (A) of exposing hydrous acetic acid having a water content of 1 to 15 mass % to the pyridine-ring-containing chelate resin which has undergone the adsorption step, thereby yielding an eluate containing the by-produced carboxylic acid mixture, (3) an elution step (B) of exposing water or hydrous acetic acid having a water content of 20 mass % or more to the pyridine-ring-containing chelate resin which has undergone the elution step (A), thereby yielding an eluate containing catalyst-derived heavy metal ions and bromide ions, and (4) a displacement step of exposing hydrous acetic acid having a water content of 1 to 15 mass % to the pyridine-ring-containing chelate resin which has undergone the elution step (B), serving as a displacement liquid, thereby regenerating the resin;

[2] the method for producing terephthalic acid as described in [1] above, wherein hydrous acetic acid is recovered from the mother liquor which has undergone the adsorption step, from the eluate obtained through the elution step (A), and from the displacement liquid employed in the displacement step, and the recovered hydrous acetic acid is reused in the liquid-phase oxidation reaction as at least a portion of hydrous acetic acid having a water content of 1 to 15 mass %;

[3] the method for producing terephthalic acid as described in [1] or [2] above, wherein hydrous acetic acid is recovered from the mother liquor which has undergone the adsorption step, from the eluate obtained through the elution step (A), and from the displacement liquid employed in the displacement step, and the recovered hydrous acetic acid is reused in the elution step (A) as at least a portion of hydrous acetic acid having a water content of 1 to 15 mass %;

[4] the method for producing terephthalic acid as described in any one of [1] to [3] above, wherein hydrous acetic acid is recovered from the mother liquor which has undergone the adsorption step, from the eluate obtained through the elution step (A), and from the displacement liquid employed in the displacement step, and the recovered hydrous acetic acid is reused in the displacement step as a displacement liquid;

[5] the method for producing terephthalic acid as described in any one of [1] to [4] above, wherein the eluate obtained through the elution step (B) is returned to the liquid-phase oxidation reaction, and reused as at least a portion of the catalyst;

[6] the method for producing terephthalic acid as described in any one of [1] to [5] above, wherein a regenerated pyridine-ring-containing chelate resin which has been obtained through the displacement step is reused in the adsorption step as the pyridine-ring-containing chelate resin;

[7] the method for producing terephthalic acid as described in any one of [1] to [6] above, wherein the hydrous acetic acid having a water content of 1 to 15 mass % and employed in the elution step (A) contains bromide ions in an amount of 1 to 1,000 mass ppm;

[8] the method for producing terephthalic acid as described in any one of [1] to [7] above, wherein the hydrous acetic acid having a water content of 1 to 15 mass % and employed in the displacement step as a displacement liquid contains bromide ions in an amount of 1 to 1,000 mass ppm;

[9] the method for producing terephthalic acid as described in any one of [1] to [8] above, wherein, in the adsorption step, the ratio "amount by mole of bromide ions in the mother liquor/total amount by mole of heavy metal ions in the mother liquor" is regulated to 1.6 to 2.5; and

[10] the method for producing terephthalic acid as described in any one of [1] to [9] above, wherein when Q represents the total amount (g) of hydrous acetic acid having a water content of 1 to 15 mass % supplied in the elution step (A), and V represents the volume (mL) of a pyridine-ring-containing chelate resin layer, the ratio Q/V is 0.5 to 10.

Effects of the Invention

In the method for producing of terephthalic acid, a by-produced carboxylic acid mixture can be effectively separated from catalyst-derived heavy metal ions and bromide ions, and the thus-recovered heavy metal ions and bromide ions can be reused, as it is, as a catalyst in liquid-phase oxidation reaction. Therefore, terephthalic acid can be produced stably in a more economically advantageous manner while high reaction yield is maintained over a long period of time.

BRIEF DESCRIPTION OF THE DRAWING

FIG. 1 shows an exemplary process for producing terephthalic acid.

DESCRIPTION OF REFERENCE NUMERALS

1: Reactor
2: Crystallization step
3: Solid-liquid separator
4: Mother liquor receiving tank
5: Pyridine-ring-containing chelate resin column
6: Hydrobromic acid tank
7: Tank for storing hydrous acetic acid having a water content of about 12 mass % (also called "displacement liquid tank")
8: Tank for storing hydrous acetic acid having a water content of about 35 mass %
9: Intermediate tank
10: Raw material tank
11: Conduit for cake of crude terephthalic acid crystals
12: Conduit for mother liquor
13: Conduit for hydrobromic acid
14: Conduit for prepared mother liquor
15: Conduit over column
16: Conduit under column
17: Conduit for purged liquid
18: Conduit for hydrous acetic acid having a water content of about 12 mass % (also called "displacement liquid conduit")
19: Conduit for hydrous acetic acid having a water content of about 35 mass %
20: Conduit for recovered catalyst liquid
21: Conduit for recovered catalyst liquid
22: Conduit for raw material mixture

BEST MODES FOR CARRYING OUT THE INVENTION

In the present invention, firstly, a p-phenylene compound is subjected to liquid-phase oxidation reaction by use of a molecular-oxygen-containing gas in the presence of a catalyst at least containing a heavy metal compound and a bromine compound, and hydrous acetic acid having a water content of 1 to 15 mass % (preferably 1 to 12 mass %, more preferably 1 to 9 mass %), to thereby yield a slurry (hereinafter the thus-obtained slurry may be referred to as an "oxidation reaction slurry"). As used herein, the term "p-phenylene compound" refers to a phenylene compound having substituents at positions 1 and 4 of the benzene ring. Examples of such a substituent include alkyl groups such as methyl, ethyl, propyl, and butyl. A particularly preferred p-phenylene compound is p-xylene.

At least one of a cobalt compound and a manganese compound is essentially employed as a heavy metal compound (i.e., a catalyst component), and optionally, for example, a nickel compound, a cerium compound, or a zirconium compound may be employed together with such an essential heavy metal compound. Examples of the cobalt compound, manganese compound, nickel compound, cerium compound, and zirconium compound include organic acid salts, hydroxides, halides, and carbonates of the respective metals. Particularly, acetic acid salts and bromides of the respective metals are preferably employed. Specific examples of such a heavy metal compound include cobalt acetate, cobalt hydroxide, cobalt fluoride, cobalt chloride, cobalt bromide, cobalt iodide, cobalt carbonate, manganese acetate, manganese hydroxide, manganese fluoride, manganese chloride, manganese bromide, manganese iodide, manganese carbonate, nickel acetate, nickel hydroxide, nickel fluoride, nickel chloride, nickel bromide, nickel iodide, nickel carbonate, cerium acetate, cerium hydroxide, cerium fluoride, cerium chloride, cerium bromide, cerium iodide, cerium carbonate, zirconium acetate, zirconium hydroxide, zirconium fluoride, zirconium chloride, zirconium bromide, zirconium iodide, and zirconium carbonate.

No particular limitation is imposed on the bromine compound employed as a catalyst component, so long as it dissolves in hydrous acetic acid and generates bromide ions in the reaction system. Examples of the bromine compound include inorganic bromine compounds such as hydrogen bromide, sodium bromide, and cobalt bromide; and organic bromine compounds such as bromoacetic acid and tetrabromoethane. Of these, hydrogen bromide, cobalt bromide, and manganese bromide are preferably employed. More preferably, hydrobromic acid prepared by dissolving hydrogen bromide in an aqueous solution is employed.

The liquid-phase oxidation reaction is preferably performed at 160 to 230° C., more preferably 180 to 210° C. When the reaction temperature falls within the above range, the amount of a reaction intermediate remaining in the oxidation reaction slurry can be reduced, and excessive loss of hydrous acetic acid having a water content of 1 to 15 mass % (i.e., a solvent) by combustion is prevented. No particular limitation is imposed on the reaction pressure, so long as the reaction system can be maintained in a liquid phase at the aforementioned reaction temperature. Generally, the reaction pressure is preferably 0.78 to 3.04 MPa, more preferably 0.98 to 1.86 MPa.

Examples of a molecular-oxygen-containing gas include air, oxygen gas diluted with an inert gas, and oxygen-enriched air. Generally, air is preferred, from the viewpoints of facility and cost.

Preferably, the oxidation reaction slurry obtained through the aforementioned liquid-phase oxidation reaction is fed to the subsequent reactor connected in series, so as to thoroughly complete oxidation reaction by use of a molecular-oxygen-containing gas.

The thus-obtained oxidation reaction slurry is subjected to pressure reduction and cooling (35 to 140° C.) through flash evaporation in one or more stages in a crystallization step employing one or more crystallization tanks, to thereby thoroughly crystallize crude terephthalic acid, and then the slurry is fed to the below-described solid-liquid separator.

The oxidation reaction slurry obtained through the aforementioned liquid-phase oxidation reaction is separated into crude terephthalic acid crystals and a mother liquor by means of a solid-liquid separator. This solid-liquid separation is generally performed at atmospheric pressure. No particular limitation is imposed on the separation temperature, but this separation is generally performed at a temperature lower than the boiling point of hydrous acetic acid at atmospheric pressure (e.g., 35 to 110° C.). Examples of the solid-liquid separator include a centrifugal separator, a centrifugal filter, and a vacuum filter. This solid-liquid separation is preferably performed so that the crystal content of the mother liquor is 1 mass % or less, more preferably 0.1 mass % or less.

The thus-obtained crude terephthalic acid crystals may be appropriately subjected to a known purification process, such as catalytic hydrogenation (see, for example, Japanese Patent Publication (kokoku) No. S41-16860), oxidation treatment, or recrystallization, to thereby yield terephthalic acid crystals of high purity.

<Adsorption Step>

The mother liquor recovered through separation of crude terephthalic acid crystals from the oxidation reaction slurry by the aforementioned procedure contains catalyst-derived heavy metal ions and bromide ions, and a by-produced carboxylic acid mixture. These heavy metal ions are ions of the heavy metals constituting the aforementioned heavy metal compounds. The by-produced carboxylic acid mixture includes aromatic polycarboxylic acids each having carboxyl groups which are ortho to each other. Examples of such an aromatic polycarboxylic acid include trimellitic acid compounds (e.g., trimellitic acid, hemimellitic acid, and 5-methyltrimellitic acid); pyromellitic acid; and phthalic acid compounds (e.g., phthalic acid, 3-methylphthalic acid, and 4-methylphthalic acid). The mother liquor contains, in addition to the aforementioned ions and by-produced carboxylic acid mixture, various organic compounds (e.g., terephthalic acid, acetic acid, unreacted raw materials, reaction intermediates, and reaction by-products), and a considerable amount of water (i.e., a reaction product).

In the present invention, the ratio "amount by mole of bromide ions in the mother liquor/total amount by mole of heavy metal ions in the mother liquor" (hereinafter the ratio may be referred to as "the bromide ratio (of the mother liquor)") is regulated, and then a pyridine-ring-containing chelate resin is exposed to the mother liquor, to thereby selectively adsorb catalyst-derived heavy metal ions, bromide ions, and a by-produced carboxylic acid mixture on the pyridine-ring-containing chelate resin, whereby a liquid (hereinafter the thus-obtained liquid may be referred to as a "residual mother liquor") is recovered [adsorption step]. When crude terephthalic acid crystals recovered through separation by means of a solid-liquid separator are washed with water or hydrous acetic acid, a liquid obtained through this washing may be mixed with the mother liquor, and the resultant mixture may be subjected to the adsorption step.

The pyridine-ring-containing chelate resin employed in the present invention is an anion-exchange-type chelate resin having a pyridine ring and obtained through polymerization of 4-vinylpyridine and divinylbenzene serving as main raw materials. In general, a chelate resin is a water-insoluble polymer base having a ligand which can coordinate with metal ions to form a complex, and exhibits a function of selectively adsorbing/separating specific metal ions. Particularly, a 'pyridine-ring-containing' chelate resin is advantageous in that it effectively adsorbs heavy metal ions. Such a pyridine-ring-containing chelate resin may be a commercially available one. Examples of commercially available pyridine-ring-containing chelate resins include "REILLEX (registered trademark) 425 Polymer" (trade name, product of Reilly) and "Sumichelate (registered trademark) CR-2" (trade name, product of Sumitomo Chemical Co., Ltd.).

No particular limitation is imposed on the method for exposing the mother liquor to a pyridine-ring-containing chelate resin, and, for example, the chelate resin is impregnated with the mother liquor, or the mother liquor is caused to pass through the chelate resin. From the viewpoint of adsorption efficiency, more preferably, the mother liquor is caused to pass through a pyridine-ring-containing chelate resin. From the viewpoints of heat resistance and adsorption performance of a pyridine-ring-containing chelate resin, the chelate resin must be heated to 35 to 140° C. before being exposed to the mother liquor. The chelate resin is preferably heated to 45 to 130° C., more preferably 70 to 120° C., much more preferably 85 to 110° C.

The residual mother liquor obtained by exposing the mother liquor to a pyridine-ring-containing chelate resin contains hydrous acetic acid having a water content of 1 to 15 mass %. Therefore, preferably, the hydrous acetic acid is recovered from the residual liquid through, for example, distillation, and at least a portion of the thus-recovered hydrous acetic acid is reused in liquid-phase oxidation reaction, or employed as a displacement liquid for the below-described regeneration of the pyridine-ring-containing chelate resin.

In the present invention, the mother liquor obtained through liquid-phase oxidation reaction and solid-liquid separation generally has a water content of 7 to 16 mass %. Therefore, when the mother liquor is applied to a pyridine-ring-containing chelate resin column, in many cases, the water content of the mother liquor is not particularly required to be regulated. However, when the water content of the mother liquor is increased by, for example, mixing the mother liquor with a liquid obtained through the aforementioned washing of crude terephthalic acid crystals recovered by solid-liquid separation, the water content is preferably regulated to 16 mass % or less (more preferably 1 to 14 mass %, much more preferably 5 to 12 mass %) through, for example, distillation. When the water content of the mother liquor exceeds 16 mass %, in the adsorption step, catalyst-derived heavy metal ions and bromide ions and a by-produced carboxylic acid mixture are less likely to be sufficiently adsorbed on a pyridine-ring-containing chelate resin.

The pyridine-ring-containing chelate resin which has not undergone any preliminary treatment may be exposed to the mother liquor. However, preferably, the mother liquor is brought into contact with a bromide-type chelate resin prepared by exposing a pyridine-ring-containing chelate resin to, for example, an acetic acid solution containing bromide ions in advance. No particular limitation is imposed on the method for preparing a bromide-type pyridine-ring-containing chelate resin, and, for example, the chelate resin may be prepared by exposing a pyridine-ring-containing chelate resin to an aqueous solution of any of the aforementioned bromine compounds (e.g., sodium bromide and hydrogen bromide) or a liquid mixture of the aqueous solution and acetic acid, followed by removal of excess bromide through washing with glacial acetic acid or hydrous acetic acid having a water content of 15 mass % or less. This washing is preferably performed with hydrous acetic acid having a water content lower than that of the mother liquor.

From the viewpoint of efficient elution of a by-produced carboxylic acid mixture adsorbed on a pyridine-ring-containing chelate resin, the bromide ratio of the mother liquor is 0.6 to 3, preferably 0.7 to 2.8, more preferably 0.9 to 2.5, much more preferably 1.6 to 2.5, particularly preferably 2 to 2.5. When the bromide ratio is high, percent adsorption of the aforementioned heavy metal ions is increased, and percent adsorption of a by-produced carboxylic acid mixture tends to be reduced. Therefore, when the bromide ratio is increased particularly in the adsorption step, in the below-described elution step (A), a by-produced carboxylic acid mixture can be effectively separated from catalyst components (i.e., heavy metal ions and bromide ions). The bromide ratio is regulated by, for example, adding, to the mother liquor, an aqueous solution of any of the aforementioned bromine compounds (e.g., hydrobromic acid) serving as a bromide source.

<Elution Steps (A) and (B)>

In the present invention, the pyridine-ring-containing chelate resin which has undergone the aforementioned adsorption step is subjected to an elution step (A); i.e., a step of exposing the resin to hydrous acetic acid having a water content of 1 to 15 mass % (preferably 1 to 12 mass %, more preferably 1 to 9 mass %), thereby selectively eluting a by-produced carboxylic acid mixture, and then is subjected to an elution step (B); i.e., a step of exposing the resin to water or hydrous acetic acid having a water content of 20 mass % or more, thereby recovering catalyst-derived heavy metal ions and bromide ions.

The pyridine-ring-containing chelate resin which has undergone the aforementioned adsorption step contains, in addition to catalyst-derived heavy metal ions and bromide ions, a by-produced carboxylic acid mixture. When the pyridine-ring-containing chelate resin is subjected to the elution step (B) without being subjected to the elution step (A), so as to recover the heavy metal ions and bromide ions (i.e., catalyst components), the by-produced carboxylic acid mixture is contained in the catalyst components. In such a case, when the catalyst components are returned to and reused in the reaction system, the concentration of the by-produced carboxylic acid mixture is gradually increased in the reaction system and the mother liquor, which causes deactivation of the catalyst. Such a process results in an economic disadvantage when being put into practice on an industrial scale. In order to suppress an increase in concentration of the by-produced carboxylic acid mixture, the elution step (A) is required; i.e., the by-produced carboxylic acid mixture is selectively eluted, with heavy metal ions and bromide ions being adsorbed on the pyridine-ring-containing chelate resin.

The hydrous acetic acid having a water content of 1 to 15 mass % and employed in the elution step (A) preferably contains bromide ions in an amount of 1 to 1,000 mass ppm, more preferably 10 to 1,000 mass ppm, for rapidly eluting the by-produced carboxylic acid mixture adsorbed on the pyridine-ring-containing chelate resin. In the elution step (A), there may be employed acetic acid (water content: 4 to 11 mass %, bromide ion content: 1 to 50 mass ppm) recovered from the bottom of a distillation column upon removal of water (through evaporation) from the residual mother liquor obtained through the adsorption step, an eluate obtained through the elution step (A), or a displacement liquid employed in the below-described displacement step.

When Q represents the total amount (g) of hydrous acetic acid supplied in the elution step (A), and V represents the volume (mL) of a pyridine-ring-containing chelate resin layer, the ratio Q/V is preferably 0.5 to 10, more preferably 1 to 6, much more preferably 3 to 4.5. When the ratio Q/V falls within the above range, the by-produced carboxylic acid mixture can be effectively and selectively eluted from the pyridine-ring-containing chelate resin.

Preferably, hydrous acetic acid having a water content of 1 to 15 mass % is recovered, through distillation or a similar technique, from the eluate obtained through the elution step (A), which contains the by-produced carboxylic acid mixture, and at least a portion of the thus-recovered hydrous acetic acid is reused in liquid-phase oxidation reaction, or employed in the elution step (A) or in the below-described displacement step.

In the elution step (B), metal impurities other than catalyst-derived heavy metal ions and bromide ions are not virtually adsorbed on the pyridine-ring-containing chelate resin. Therefore, through exposing the resin to water or hydrous acetic acid having a water content of 20 mass % or more (preferably 20 to 70 mass %, more preferably 25 to 50 mass %, much more preferably 25 to 40 mass %), hydrous acetic acid which contains heavy metal ions and bromide ions, and which can be reused, as it is, in liquid-phase oxidation reaction (hereinafter the thus-obtained hydrous acetic acid may be referred to as a "recovered catalyst liquid") can be produced.

Alternatively, a condensate (water content: 20 to 50 mass %) recovered in liquid-phase oxidation reaction by means of a reflux condenser attached to the reactor may be employed in the elution step (B) as hydrous acetic acid.

<Displacement Step>

In this step, from the viewpoint of adsorption efficiency of catalyst components, the pyridine-ring-containing chelate resin which has undergone the elution step (B) is brought into contact with a displacement liquid; i.e., hydrous acetic acid having a water content of 1 to 15 mass % (preferably 1 to 12 mass %, more preferably 1 to 9 mass %), to thereby regenerate the pyridine-ring-containing chelate resin. The thus-regenerated pyridine-ring-containing chelate resin can be reused in the adsorption step. Through the displacement step, the water content of hydrous acetic acid present around the chelate resin is reduced to a level equal to the water content of the displacement liquid, so that heavy metal ions and bromide ions are rapidly adsorbed on the chelate resin in the subsequent adsorption step. In contrast, when the displacement step is not performed, since the chelate resin layer is surrounded by hydrous acetic acid having a high water content immediately after the elution step (B), in the adsorption step, adsorption efficiency of catalyst components is reduced at an early stage of exposure of the chelate resin to the mother liquor, and percent recovery of the catalyst components is reduced, resulting in an economic disadvantage.

In order to facilitate adsorption of cobalt ions, manganese ions, and bromide ions on the pyridine-ring-containing chelate resin, more preferably, hydrous acetic acid having a water content of 1 to 15 mass % and containing bromide ions in an amount of 1 to 1,000 mass ppm is employed as a displacement liquid.

There may be employed, as a displacement liquid, acetic acid (water content: 4 to 11 mass %, bromide ion content: 1 to 50 mass ppm) recovered from the bottom of a distillation column upon removal of water (through evaporation) from the residual mother liquor obtained through the adsorption step, the eluate obtained through the elution step (A), or the displacement liquid employed in the displacement step.

The overall flow of the method of the present invention will next be briefly described with reference to FIG. 1, which shows an exemplary process for producing terephthalic acid. However, the present invention is not limited to the process shown in FIG. 1.

As shown in FIG. 1, a mixture of raw materials (a p-phenylene compound, a heavy metal compound, a bromine compound, and hydrous acetic acid) is fed through a conduit 22 to a reactor 1, and liquid-phase oxidation reaction is performed in the presence of a molecular-oxygen-containing gas. The reaction product is in the form of slurry obtained through crystallization of a portion of crude terephthalic acid. The reaction product is subjected to pressure reduction and cooling through flash evaporation in several stages in a crystallization step 2, followed by separation by means of a solid-liquid separator 3, to thereby yield a cake of crude terephthalic acid crystals. The thus-obtained cake is transferred through a conduit 11. The mother liquor recovered through separation by means of the solid-liquid separator 3 is fed via a conduit 12 to a mother liquor receiving tank 4, and hydrobromic acid is fed from a hydrobromic acid tank 6 through a conduit 13 to the mother liquor receiving tank 4, to thereby appropriately regulate the bromide ratio of the mother liquor. Subsequently, the mother liquor is caused to pass through conduits 14 and 15, and then subjected to the adsorption step; i.e., the mother liquor is introduced to a pyridine-ring-containing chelate resin column 5 through the top of the column and caused to pass therethrough. A substance which is not adsorbed on the pyridine-ring-containing chelate resin is discharged from the bottom of the column, and then purged via conduits 16 and 17. The substance is appropriately subjected to, for example, distillation for recovery of hydrous acetic acid, and the thus-recovered hydrous acetic acid is transferred (for reuse) to a raw material tank 10 or a tank 7 for storing hydrous acetic acid having a water content of about 12 mass %.

The pyridine-ring-containing chelate resin which has undergone the adsorption step is subjected to the elution step (A). Specifically, hydrous acetic acid having a water content of about 12 mass % is fed from the tank 7 through a conduit 18 and the conduit 15, and introduced to the pyridine-ring-containing chelate resin column 5 through the top of the column and caused to pass therethrough. An eluate containing a by-produced carboxylic acid mixture is discharged from the bottom of the column, and then purged via the conduits 16 and 17. The eluate is appropriately subjected to, for example, distillation for recovery of hydrous acetic acid, and the thus-recovered hydrous acetic acid is transferred (for reuse) to the raw material tank 10 or the tank 7 for storing hydrous acetic acid having a water content of about 12 mass %.

After completion of the elution step (A), the elution step (B) is carried out. Specifically, hydrous acetic acid having a water content of about 35 mass % is fed from a tank 8 through a conduit 19 and the conduit 16, and introduced to the pyridine-ring-containing chelate resin column 5 so as to pass therethrough for elution of heavy metal ions and bromide ions adsorbed on the pyridine-ring-containing chelate resin. The thus-recovered catalyst liquid is transferred through a conduit 20 to an intermediate tank 9. Subsequently, the recovered catalyst liquid is fed through a conduit 21 to the raw material tank 10, and reused as a catalyst for liquid-phase oxidation reaction.

After completion of the elution step (B), the displacement step is carried out. Specifically, hydrous acetic acid having a water content of about 12 mass %, serving as a displacement liquid, is fed from the displacement liquid tank 7 through the conduit 18 and the conduit 15, and introduced to the pyridine-ring-containing chelate resin column 5 so as to pass therethrough. The resultant eluate is purged via the conduits 16 and 17. The eluate is appropriately subjected to, for example, distillation for recovery of hydrous acetic acid, and the thus-recovered hydrous acetic acid is transferred (for reuse) to the raw material tank 10 or the tank 7 for storing hydrous acetic acid having a water content of about 12 mass %. After completion of the displacement step, the aforementioned adsorption step may be carried out.

EXAMPLES

The present invention will next be described in more detail by way of examples, which should not be construed as limiting the invention thereto.

<Preliminary Treatment of Pyridine-Ring-Containing Chelate Resin>

In each of the Examples and the Comparative Example, there was employed a pyridine-ring-containing chelate resin prepared through the following procedure: an acetic acid solution (200 mL) containing 10 mass % hydrobromic acid was caused to pass through a pyridine-ring-containing chelate resin ["Sumichelate (registered trademark) CR-2" (trade name, product of Sumitomo Chemical Co., Ltd.)] so as to prepare a bromide-type pyridine-ring-containing chelate resin, and excess hydrobromic acid was rinsed out the chelate resin with an acetic acid solution having a water content of 12 mass %.

<Method for Determining Heavy Metal Ion Concentration>

Heavy metal ion concentration was determined by means of an atomic absorption spectrophotometer having the following specification.

Model: Polarized Zeeman atomic absorption spectrophotometer Z-2300 (product of Hitachi High-Technologies Corporation)

Wavelength: Cobalt ion: 240.7 nm, Manganese ion: 279.6 nm

Flame: Acetylene-air

Determination method: An appropriate amount of a sample is placed in a 100-mL glass container (mass of the sample is measured by means of a balance), and the sample is diluted with pure water and 20 mass % hydrochloric acid (constant boiling point, iron-free) for accurate analysis (about 2 mL) so that the concentration of heavy metal ions to be measured is about 1 ppm (the mass of the diluted sample is measured for determination of a dilution factor). The heavy metal ion concentration of the diluted sample is determined on the basis of a calibration curve prepared by use of standard samples having heavy metal ion concentrations of 0 ppm, 1 ppm, and 2 ppm. The heavy metal ion concentration of the undiluted sample is determined by multiplying the heavy metal ion concentration of the diluted sample by the dilution factor.

<Method for Determining Bromide Ion Concentration>

Bromide ion concentration was determined under the following conditions.

Titrator: Automatic potentiometric titrator AT-510 (product of Kyoto Electronics Manufacturing Co., Ltd.)

Titration liquid: 1/250 N aqueous silver nitrate solution

Detection electrodes:

Composite glass electrode C-172

Silver electrode M-214

Temperature compensation electrode T-111

Determination method: A Teflon (registered trademark) stirrer chip is placed in a 200-mL beaker, and an appropriate amount of a sample is placed therein (the mass of the sample is measured by means of a balance). Pure water is added to the beaker so that the volume of the liquid in the beaker is about 150 mL, and 60 mass % nitric acid (about 2 mL) is added thereto. Bromide ion concentration is determined through precipitation titration by means of the aforementioned automatic potentiometric titrator.

<Method for Determining By-Produced Carboxylic Acid Mixture Concentration>

Concentration of each of the aforementioned phthalic acid compounds and trimellitic acid compounds was determined through gas chromatography under the following conditions.
Model: Agilent 6890N (product of Agilent Technologies)
Column employed: DB-1 (product of Agilent Technologies)
Column temperature: 100 to 280° C.
Detector: Flame ionization detector (FID)

Percent recovery of catalyst components and percent inclusion of a by-produced carboxylic acid mixture were calculated through the following methods.

<Cobalt Ion>

Percent recovery of cobalt ions was determined by calculating the ratio (%) of the amount of cobalt ions contained in a recovered catalyst liquid to that of cobalt ions contained in a mother liquor.

<Manganese Ion>

Percent recovery of manganese ions was determined by calculating the ratio (%) of the amount of manganese ions contained in the recovered catalyst liquid to that of manganese ions contained in the mother liquor.

<Bromide Ion>

Percent recovery of bromide ions was determined by calculating the ratio (%) of the amount of bromide ions contained in the recovered catalyst liquid to that of bromide ions contained in the mother liquor.

<By-Produced Carboxylic Acid Mixture>

Percent inclusion of a by-produced carboxylic acid mixture was determined by calculating the ratio (%) of the amount of a phthalic acid compound or trimellitic acid compound contained in the recovered catalyst liquid to that of a phthalic acid compound or trimellitic acid compound contained in the mother liquor.

Example 1 p-Xylene was subjected to liquid-phase oxidation reaction (reaction temperature: 200° C., reaction pressure: 1.62 MPa) by use of air in hydrous acetic acid having a water content of 9 mass % in the presence of cobalt acetate, manganese acetate, and hydrobromic acid, to thereby yield a slurry containing crude terephthalic acid. Subsequently, the slurry was subjected to a crystallization step, followed by pressure release and cooling to 100° C. Thereafter, the terephthalic acid was removed through solid-liquid separation with a glass filter, to thereby recover crude terephthalic acid crystals and a mother liquor of about 80° C. The mother liquor was found to contain cobalt ions in an amount of 610 mass ppm, manganese ions in an amount of 360 mass ppm, bromide ions in an amount of 810 mass ppm, trimellitic acid compounds in an amount of 2,500 mass ppm, phthalic acid compounds in an amount of 2,100 mass ppm, and water in an amount of 12 mass %. The bromide ratio of the mother liquor was found to be 0.6.

The above-preliminarily treated pyridine-ring-containing chelate resin (90 mL) was charged into a double-tube glass column. Hot water of 80° C. was circulated through a jacket of the pyridine-ring-containing chelate resin column, to thereby maintain the pyridine-ring-containing chelate resin at 80° C.

The aforementioned mother liquor was introduced to the pyridine-ring-containing chelate resin column through the top of the column and was caused to pass downward therethrough at a flow rate of 360 g/hour for 50 minutes [adsorption step]. Thereafter, hydrous acetic acid having a water content of 12 mass % was introduced to the column through the top and caused to pass downward therethrough at a flow rate of 360 g/hour for 20 minutes (Q/A=120 g/90 mL=about 1.33) [elution step (A)]. After completion of the elution step (A), hydrous acetic acid having a water content of 35 mass % was introduced to the column through the bottom and caused to pass upward therethrough at a flow rate of 360 g/hour for 90 minutes [elution step (B)]. After completion of the elution step (B), an displacement liquid (hydrous acetic acid having a water content of 12 mass %) was introduced to the column through the top and caused to pass downward therethrough at the same flow rate as described above for 20 minutes [displacement step]. A cycle consisting of the adsorption step, the elution step (A), the elution step (B), and the displacement step (and return to the adsorption step) was repeated at 180 minutes/cycle.

Hydrous acetic acid having a water content of about 12 mass % was recovered, through distillation, from the residual mother liquor obtained through the adsorption step, from the eluate obtained through the elution step (A), and from the displacement liquid employed in the displacement step. The thus-recovered hydrous acetic acid was reused as hydrous acetic acid in the liquid-phase oxidation reaction, as hydrous acetic acid in the elution step (A), and as a displacement liquid in the displacement step. Also, a catalyst liquid recovered through the elution step (B) and containing cobalt ions, manganese ions, and bromide ions was reused as a catalyst for liquid-phase oxidation reaction.

Table 1 shows data of percent recovery of cobalt ions, manganese ions, and bromide ions, and percent inclusion of phthalic acid compounds and trimellitic acid compounds, as determined by use of a catalyst liquid recovered on day 4 of the experiment.

The experiment was further continued. However, liquid-phase oxidation reaction was effectively performed without reducing catalytic activity.

TABLE 1

|  | Percent recovery |
| --- | --- |
| Cobalt ions | 88% |
| Manganese ions | 68% |
| Bromide ions | 92% |
|  | Percent inclusion |
| Trimellitic acid compounds | 50% |
| Phthalic acid compounds | 9% |

Comparative Example 1

The experiment and measurement were performed in the same manner as employed in Example 1, except that the elution step (A) was not performed, and the cycle consisting of the adsorption step, the elution step (B), and the displacement step (and return to the adsorption step) was repeated at 160 minutes/cycle. The results are shown in Table 2.

The experiment was further continued. The catalytic activity was gradually reduced, and the yield of terephthalic acid produced through liquid-phase oxidation reaction was considerably reduced.

TABLE 2

|  | Percent recovery |
| --- | --- |
| Cobalt ions | 89% |
| Manganese ions | 79% |
| Bromide ions | 93% |

TABLE 2-continued

| | Percent inclusion |
|---|---|
| Trimellitic acid compounds | 77% |
| Phthalic acid compounds | 38% |

Example 2

The experiment and measurement were performed in the same manner as employed in Example 1, except that the elution step (A) was performed for 60 minutes (Q/A=360 g/90 mL=4), and the cycle consisting of the adsorption step, the elution step (A), the elution step (B), and the displacement step (and return to the adsorption step) was repeated at 220 minutes/cycle. The results are shown in Table 3.

The experiment was further continued. However, liquid-phase oxidation reaction was effectively performed without reducing catalytic activity.

TABLE 3

| | Percent recovery |
|---|---|
| Cobalt ions | 88% |
| Manganese ions | 67% |
| Bromide ions | 91% |
| | Percent inclusion |
| Trimellitic acid compounds | 34% |
| Phthalic acid compounds | 5% |

Example 3

The experiment and measurement were performed in the same manner as employed in Example 1, except that hydrobromic acid was added to the recovered mother liquor so as to attain a bromide ratio of 0.9, and then the mother liquor was subjected to the adsorption step. The results are shown in Table 4.

The experiment was further continued. However, liquid-phase oxidation reaction was effectively performed without reducing catalytic activity.

TABLE 4

| | Percent recovery |
|---|---|
| Cobalt ions | 96% |
| Manganese ions | 72% |
| Bromide ions | 92% |
| | Percent inclusion |
| Trimellitic acid compounds | 43% |
| Phthalic acid compounds | 7% |

Example 4

The experiment and measurement were performed in the same manner as employed in Example 1, except that hydrobromic acid was added to the recovered mother liquor so as to attain a bromide ratio of 1.2, and then the mother liquor was subjected to the adsorption step. The results are shown in Table 5.

The experiment was further continued. However, liquid-phase oxidation reaction was effectively performed without reducing catalytic activity.

TABLE 5

| | Percent recovery |
|---|---|
| Cobalt ions | 98% |
| Manganese ions | 77% |
| Bromide ions | 92% |
| | Percent inclusion |
| Trimellitic acid compounds | 38% |
| Phthalic acid compounds | 6% |

Example 5

The experiment and measurement were performed in the same manner as employed in Example 1, except that hydrobromic acid was added to the recovered mother liquor so as to attain a bromide ratio of 1.5, and then the mother liquor was subjected to the adsorption step. The results are shown in Table 6.

The experiment was further continued. However, liquid-phase oxidation reaction was effectively performed without reducing catalytic activity.

TABLE 6

| | Percent recovery |
|---|---|
| Cobalt ions | 99% |
| Manganese ions | 81% |
| Bromide ions | 91% |
| | Percent inclusion |
| Trimellitic acid compounds | 32% |
| Phthalic acid compounds | 5% |

Example 6

The procedure of Example 1 was repeated. However, in Example 6, a pyridine-ring-containing chelate resin "REILLEX (registered trademark) 425 Polymer" (trade name, product of Reilly) (90 mL) was used; the mother liquor was fed to the adsorption step after the bromide ratio had been adjusted to 2.5 through addition of hydrobromic acid; and a cycle [adsorption step (120 min), elution step (A) (20 min, Q/A=120 g/90 mL=about 1.33), elution step (B) (80 min), and displacement step (20 min)] was repeated at 240 minutes/cycle. Also, hydrous acetic acid (water content: 8 mass %, bromide ion level: 10 mass ppm) recovered from the bottom of a distillation column upon removal of water (through evaporation) at 125° C. (ambient pressure) from an eluate obtained through the elution step (A) was employed as the hydrous acetic acid in the elution step (A) and as the displacement liquid in the displacement step. Table 7 shows data of percent recovery of cobalt ions, manganese ions, and bromide ions, and percent inclusion of phthalic acid compounds and trimellitic acid compounds, as determined by use of a catalyst liquid recovered on day 180 of the experiment.

The experiment was further continued. However, liquid-phase oxidation reaction was effectively performed without reducing catalytic activity.

TABLE 7

| | Percent recovery |
|---|---|
| Cobalt ions | 99.9% |
| Manganese ions | 90% |
| Bromide ions | 96% |

TABLE 7-continued

| | Percent inclusion |
|---|---|
| Trimellitic acid compounds | 3% |
| Phthalic acid compounds | 0% |

Example 7

The experiment was performed in the same manner as employed in Example 6, except that the recovered mother liquor was heated to 90° C., and then subjected to the adsorption step. Table 8 shows data of percent recovery of cobalt ions, manganese ions, and bromide ions, and percent inclusion of phthalic acid compounds and trimellitic acid compounds, as determined by use of a catalyst liquid recovered on day 10 of the experiment.

The experiment was further continued. However, liquid-phase oxidation reaction was effectively performed without reducing catalytic activity.

TABLE 8

| | Percent recovery |
|---|---|
| Cobalt ions | 99.9% |
| Manganese ions | 98% |
| Bromide ions | 99% |
| | Percent inclusion |
| Trimellitic acid compounds | 1.8% |
| Phthalic acid compounds | 0% |

Example 8

The experiment was performed in the same manner as employed in Example 6, except that the recovered mother liquor was cooled to 40° C. so as to remove a precipitated solid content, and then subjected to the adsorption step, and that the pyridine-ring-containing chelate resin was employed at 40° C. Table 9 shows data of percent recovery of cobalt ions, manganese ions, and bromide ions, and percent inclusion of phthalic acid compounds and trimellitic acid compounds, as determined by use of a catalyst liquid recovered on day 7 of the experiment.

The experiment was further continued. However, liquid-phase oxidation reaction was effectively performed without reducing catalytic activity.

TABLE 9

| | Percent recovery |
|---|---|
| Cobalt ions | 84% |
| Manganese ions | 63% |
| Bromide ions | 81% |
| | Percent inclusion |
| Trimellitic acid compounds | 5% |
| Phthalic acid compounds | 0% |

As is clear from the data obtained in Examples 1 to 8, according to the method of the present invention, percent inclusion of trimellitic acid compounds is reduced to 50% or less, and percent inclusion of phthalic acid compounds is reduced to 10% or less. In addition, under certain conditions, the percent inclusion is reduced to 5% or less. Particularly when the time of the elution step (A) (i.e., Q/A) is regulated as described in Example 2, or when the bromide ratio of a mother liquor is modified before the adsorption step (Examples 3 to 5), percent inclusion of trimellitic acid compounds and phthalic acid compounds is further reduced, as compared with the case of Example 1. In contrast, according to the method of Comparative Example 1, which does not include the elution step (A) and thus is similar to a conventional production method, percent inclusion of trimellitic acid compounds is 77%, and percent inclusion of phthalic acid compounds is increased to 38%. That is, this method encounters difficulty in continuously performing liquid-phase oxidation reaction over a long period of time while reusing recovered catalyst components. In Examples 6 to 8, the bromide ratio before the adsorption step was adjusted to 2.5, and the bromide ion level of the hydrous acetic acid employed in the elution step (A) and in the displacement step was adjusted to 10 mass ppm. In these Examples, percent inclusion of trimellitic acid compounds can be successfully reduced to a very low level, and percent inclusion of phthalic acid compounds can be reduced to substantially zero. Thus, remarkable effects can be attained. When the temperature of a mother liquor is increased to 90° C. (Example 7), percent recovery of heavy metal ions is increased, and percent inclusion of trimellitic acid compounds and phthalic acid compounds is reduced.

A difference in percent inclusion of a by-produced carboxylic acid mixture by some tens % greatly affects production of terephthalic acid. Thus, the present invention realizes economically advantageous and long-term reliable production of terephthalic acid.

INDUSTRIAL APPLICABILITY

Terephthalic acid produced through the method of the present invention can be employed as, for example, a starting material for polyethylene terephthalate.

The invention claimed is:

1. A method for producing terephthalic acid comprising:
    subjecting a p-phenylene compound to a liquid-phase oxidation reaction by the use of a molecular-oxygen-containing gas in the presence of a catalyst at least containing a heavy metal compound and a bromine compound, and hydrous acetic acid having a water content of 1 to 15 mass %, to thereby yield a slurry;
    regulating the temperature of the slurry to 35 to 140° C., to thereby cause terephthalic acid to precipitate;
    removing the terephthalic acid through solid-liquid separation, to thereby recover a mother liquor; and
    recovering the catalyst from the mother liquor through a series of operations (1) to (4) for reusing at least a portion of the catalyst in the liquid-phase oxidation reaction:
    (1) an adsorption operation including regulating the amount by mole of bromide ions in the mother liquor/total amount by mole of heavy metal ions in the mother liquor ratio to 0.6 to 3, and then exposing the mother liquor to a pyridine-ring-containing chelate resin which has been heated to 35 to 140° C., so that the resin adsorbs catalyst-derived heavy metal ions and bromide ions, and also adsorbs a by-produced carboxylic acid mixture which has been by-produced through the liquid-phase oxidation reaction,
    (2) an elution operation (A) of exposing hydrous acetic acid having a water content of 1 to 15 mass % to the pyridine-ring-containing chelate resin which has undergone the adsorption operation, thereby yielding an eluate containing the by-produced carboxylic acid mixture, (3) an elution operation (B) of exposing water or hydrous acetic acid having a water content of 20 mass % or more to the pyridine-ring-containing chelate resin which has undergone the elution operation (A), thereby yielding an eluate containing catalyst-derived heavy metal ions and bromide ions, and (4) a displacement operation of exposing hydrous acetic acid having a water content of 1 to 15 mass % to the pyridine-ring-containing chelate resin which has undergone the elution operation (B), serving as a displacement liquid, thereby regenerating the resin.

2. The method for producing terephthalic acid as described in claim 1, wherein hydrous acetic acid is recovered from the mother liquor which has undergone the adsorption operation, from the eluate obtained through the elution operation (A), and from the displacement liquid employed in the displacement operation, and the recovered hydrous acetic acid is reused in the liquid-phase oxidation reaction as at least a portion of hydrous acetic acid having a water content of 1 to 15 mass %.

3. The method for producing terephthalic acid as described in claim 1, wherein hydrous acetic acid is recovered from the mother liquor which has undergone the adsorption operation, from the eluate obtained through the elution operation (A), and from the displacement liquid employed in the displacement operation, and the recovered hydrous acetic acid is reused in the elution operation (A) as at least a portion of hydrous acetic acid having a water content of 1 to 15 mass %.

4. The method for producing terephthalic acid as described in claim 1, wherein hydrous acetic acid is recovered from the mother liquor which has undergone the adsorption operation, from the eluate obtained through the elution operation (A), and from the displacement liquid employed in the displacement operation, and the recovered hydrous acetic acid is reused in the displacement operation as a displacement liquid.

5. The method for producing terephthalic acid as described in claim 1, wherein the eluate obtained through the elution operation (B) is returned to the liquid-phase oxidation reaction, and reused as at least a portion of the catalyst.

6. The method for producing terephthalic acid as described in claim 1, wherein a regenerated pyridine-ring-containing chelate resin which has been obtained through the displacement operation is reused in the adsorption operation as the pyridine-ring-containing chelate resin.

7. The method for producing terephthalic acid as described in claim 1, wherein the hydrous acetic acid having a water content of 1 to 15 mass % and employed in the elution operation (A) contains bromide ions in an amount of 1 to 1,000 mass ppm.

8. The method for producing terephthalic acid as described in claim 1, wherein the hydrous acetic acid having a water content of 1 to 15 mass % and employed in the displacement operation as a displacement liquid contains bromide ions in an amount of 1 to 1,000 mass ppm.

9. The method for producing terephthalic acid as described in claim 1, wherein, in the adsorption operation, the amount by mole of bromide ions in the mother liquor/total amount by mole of heavy metal ions in the mother liquor ratio is regulated to 1.6 to 2.5.

10. The method for producing terephthalic acid as described in claim 1, wherein when Q represents the total amount (g) of hydrous acetic acid having a water content of 1 to 15 mass % supplied in the elution operation (A), and V represents the volume (mL) of a pyridine-ring-containing chelate resin layer, the ratio Q/V is 0.5 to 10.

* * * * *